(12) United States Patent
Kulesza et al.

(10) Patent No.: US 11,253,465 B2
(45) Date of Patent: Feb. 22, 2022

(54) COMPOSITIONS AND METHODS FOR TREATING SKIN CONDITIONS

(71) Applicants: John E. Kulesza, Wethersfield, CT (US); Carlos Wambier, West Greenwich, RI (US)

(72) Inventors: John E. Kulesza, Wethersfield, CT (US); Carlos Wambier, West Greenwich, RI (US)

( * ) Notice: Subject to any disclaimer, the term of this patent is extended or adjusted under 35 U.S.C. 154(b) by 0 days.

(21) Appl. No.: 16/803,305

(22) Filed: Feb. 27, 2020

(65) Prior Publication Data
US 2020/0268642 A1 Aug. 27, 2020

Related U.S. Application Data

(60) Provisional application No. 62/811,053, filed on Feb. 27, 2019.

(51) Int. Cl.
| | | |
|---|---|---|
| *A61K 8/92* | (2006.01) | |
| *A61Q 19/08* | (2006.01) | |
| *A61K 8/37* | (2006.01) | |
| *A61K 8/34* | (2006.01) | |

(52) U.S. Cl.
CPC .............. *A61K 8/922* (2013.01); *A61K 8/347* (2013.01); *A61K 8/37* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2002/0106337 A1* | 8/2002 | Deckers | .............. | A23G 4/066 424/59 |
| 2007/0207222 A1* | 9/2007 | Yu | ..................... | A61K 47/14 424/725.1 |

OTHER PUBLICATIONS

Sigma-Aldrich, Inc. ("Tween® 20 Product Information") (Year: 2003).*

* cited by examiner

*Primary Examiner* — Quanglong N Truong
(74) *Attorney, Agent, or Firm* — Dinsmore & Shohl LLP; Weston R. Gould

(57) ABSTRACT

A composition is provided, wherein the composition includes an aqueous solvent, phenol, croton oil, and at least one saturated non-ionic ethoxylated fatty acid ester, and wherein the composition has a rate of separation of less than or equal to 0.5 mm/s. Another composition is also provided, wherein the composition includes an aqueous solvent, benzyl alcohol, ethylhexylglycerin, and at least one saturated non-ionic ethoxylated fatty acid ester. The compositions may be incorporated in to methods for treating skin conditions and cleansing skin, respectively.

21 Claims, 4 Drawing Sheets

COMPOSITIONS AND METHODS FOR TREATING SKIN CONDITIONS

CROSS-REFERENCE TO RELATED APPLICATIONS

This application claims the benefit of and priority to U.S. Provisional Application Ser. No. 62/811,053, titled "Compositions and Methods for Treating Skin Conditions," filed Feb. 27, 2019, the entire contents of which is incorporated by reference herein.

FIELD

The disclosure relates to the treatment of various skin conditions. Generally, compositions and methods are provided that treat photoaging, reduce wrinkles, and/or improve skin appearance of a user while enhancing the stability of the actives in the composition.

BACKGROUND

Animal skin serves essential roles in protecting an organism from environmental insults. Numerous specific skin functions include protection, excretion, secretion, absorption, thermoregulation, pigmentogenesis, accumulation, sensory perception, and regulation of immunological processes. The structural and chemical changes in the skin during aging reduce the effectiveness of skin to achieve each of these principal functions. Upon reaching the later stages of life, most previously robust skin functions are reduced, some by as much as 50% to 60%. The physiological changes associated with these reductions include impairment of the barrier function, decreases in epidermal and dermal thickness, decreased turnover of epidermal cells, thinning of collagen fibers, reduced numbers of keratinocytes and fibroblasts, and a reduced vascular network particularly around hair bulbs and glands. A side effect of these changes is an increase in the appearance of skin wrinkles and previously unrecognized pigmented areas.

In an effort to treat unwanted aging of skin or the appearance of aged skin, many people use chemical peels to achieve desirable outcomes such as a reduction in wrinkles or stimulate skin cell renewal. Normal skin represents a balanced cell renewal system where fully differentiated corneocytes are continually shed and replaced by new cells generated at lower skin levels. Normally this process occurs at a steady state whereby the new cells are produced at rates equivalent to the shedding of surface cells. Chemical peels offer a way to increase this rate of skin renewal. Peels function by actively removing damaged outer layers of skin, replacing it with new, more hydrated, and more robust skin cells. This can improve the texture and color of the skin, thereby providing a younger appearance. Chemical peels are also beneficial for those with facial blemishes such as acne scarring, anomalous pigmentations, or for removing actinic keratoses. When chemical peels penetrate through the epidermis and are able to damage the dermis, fibroblasts are stimulated to produce new collagen. This process can reduce wrinkles, and restore elasticity, according to the depth of injury.

Chemical peels are available in several formulations that provide superficial, medium, or deep peels. However, irritancy in the skin of the subject is a hallmark of chemical peels, even superficial peels. Traditionally, this irritancy is a source of the peeling nature of the compositions.

The deep peel, traditionally achieved by applications of phenol, croton oil, and Septisol® as an emulsifier has been used to treat deep wrinkling, remove deeper pigmentation anomalies, and treat precancerous skin growths. From 1962 to 2000, these deep peels were formulated according to Baker-Gordon's formula, which incorporated 2.1% croton oil into a mixture including phenol, water, and Septisol®. Illustrative examples of deep peels formulated according to Baker-Gordon's specifications are found in Kligman et al., *Long-Term Histologic Follow-Up of Phenol Face Peels*, Plastic and Reconstructive Surgery (May 1985). It was widely believed that phenol was the active agent in these deep peels.

However, in 1996, Dr. Gregory Hetter refuted that phenol was the active ingredient, and showed that croton oil is instead the active agent of deep peels. Through a series of publications, Hetter arrived at Hetter's formulas, which incorporated 0.1% to 1.6% croton oil into a mixture including phenol, and Septisol®. Since then, these formulas are considered to be the preferred deep peel composition. Illustrative examples of deep peels formulated according to Hetter's specifications and their results are found in Hetter, *An Examination of the Phenol-Croton Oil Peel: Part I. Dissecting the Formula*, Plastic and Reconstructive Surgery (January 2000); Hetter, *An Examination of the Phenol—Croton Oil Peel: Part II. The Lay Peelers and Their Croton Oil Formulas*, Plastic and Reconstructive Surgery (January 2000); Hetter, An Examination of the Phenol-Croton Oil Peel: Part III. The Plastic Surgeons' Role, Plastic and Reconstructive Surgery (February 2000); and Hetter, *An Examination of the Phenol—Croton Oil Peel: Part IV. Face Peel Results with Different Concentrations of Phenol and Croton Oil*, Plastic and Reconstructive Surgery (March 2000).

These phenol, croton oil, water, and Septisol® formulae, however, separate into two distinct phases within a few seconds. Due to this phase separation, surgeons are forced to swirl these mixtures together in a cup typically with the applicator used to apply the formula in an effort to maintain the suspension. As such, these typical deep peels may vary in concentration and strength throughout the procedure, leading to uneven results within and between subjects. Also, swirling phenol in cups adds the risk of splashing and increases volatility. Therefore, there exists a need for compositions and methods for treating a skin condition with deep peels utilizing alternative emulsifiers that (1) are widely available and (2) exhibit stability in suspension for long periods of time.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Compositions and methods for treating skin conditions are provided herein. In various aspects, compositions for treating skin conditions include: (i) an aqueous solvent; (ii) phenol; (iii) croton oil; and (iv) at least one saturated non-ionic ethoxylated fatty acid ester. The composition, in aspects, has a rate of separation of less than or equal to 0.5 mm/s. The composition, according to various aspects described herein, may be incorporated into a method, the method including topically applying a chemical peel to the skin of a subject.

In various aspects, a method of treating a skin condition comprises topically applying a chemical peel to the skin of a subject, wherein the chemical peel optionally includes: (i) from 50% by weight to 80% by weight water; (ii) from 20% by weight to 40% by weight phenol; (iii) from 0.1% by weight to 2.0% by weight croton oil; and (iv) from 0.1% by weight to 1.0% by weight of at least one saturated non-ionic ethoxylated fatty acid ester.

Also provided are compositions that utilize possible emulsifiers for croton oil in phenol that in the absence of croton oil and phenol are found to function well as a cleansing agent. According to various aspects, a composition for cleansing skin comprises: (i) an aqueous solvent; (ii) benzyl alcohol; (iii) ethylhexylglycerin; and (iv) at least one saturated non-ionic ethoxylated fatty acid ester.

In various aspects, a method of cleansing skin includes topically applying a skin cleansing agent to the skin of a subject, wherein the skin cleansing agent includes: (i) from 90% by weight to 99% by weight of an aqueous solvent; (ii) from 0.5% by weight to 1.5% by weight benzyl alcohol; (iii) from 0.01% by weight to 0.5% by weight ethylhexylglycerin; and (iv) from 0.1% by weight to 1.0% by weight of at least one saturated non-ionic ethoxylated fatty acid ester.

These and other objects, features, aspects, and advantages will become apparent to those of ordinary skill in the art from a reading of the following detailed description and the appended claims.

DETAILED DESCRIPTION

Figure 1:
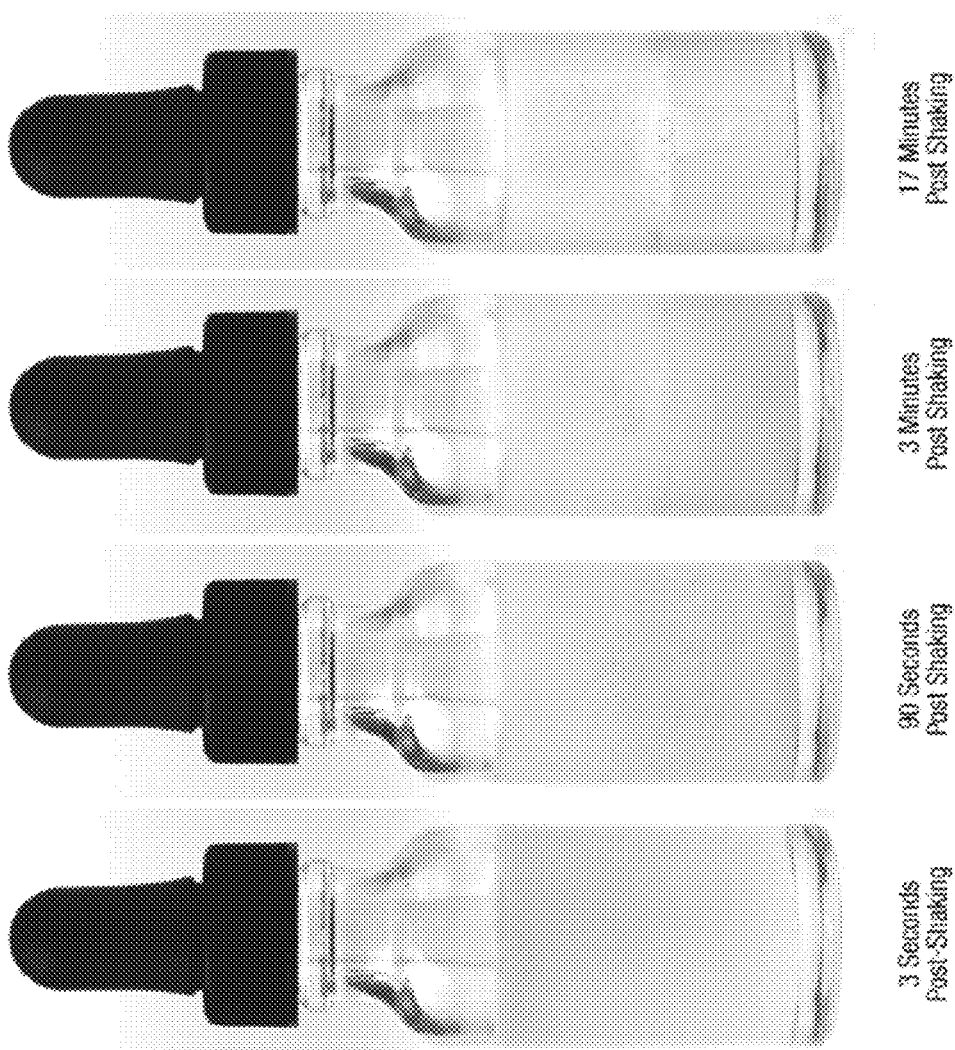
FIG. 1 illustrates the separation of phases in a typical skin peel composition according to Hetter's formula.

Provided are various compositions for treating skin conditions and/or cleansing skin and methods of using the same.

While researching various compositions for treating skin conditions, it was found that not only can prior components be effectively replaced, but that the replacement with a certain type of emulsifier, the saturated non-ionic ethoxylated fatty acid esters, also dramatically improves resistance to phase separation that was a hallmark of prior compositions. This increased stability of the resulting emulsion allows for more predictable and uniform application improving patient outcomes. As such, provided herein are compositions that exhibit improved stability in suspension relative to prior state of the art compositions.

According to various aspects, a composition suitable for use as a chemical peel for the skin of a subject includes: (i) an aqueous solvent; (ii) phenol; (iii) croton oil; and (iv) at least one saturated non-ionic ethoxylated fatty acid ester. The resulting topical composition has a rate of separation of less than or equal to 0.5 mm/s (at 25° C. and 1 atm of pressure) and is suitable for application to skin for the treatment or prevention of skin conditions such as, by way of example and not limitation, wrinkles, dry skin, dermatoses, acne, actinic keratosis, in situ squamous cell carcinomas, superficial basal-cell carcinomas, in situ melanoma, lentigo maligna, lentigos, ephelids, mottled pigmentation, solar poikiloderma, solar elastosis, acne scars, skin laxity, and other treatable skin conditions. Application of the composition, in some aspects, is achieved as per typical skin peel processes. In a method, the topically applied composition delivers the chemical peel composition to the epidermis, papillary dermis, and/or upper reticular dermis of a subject.

Also provided are compositions suitable for use as a skin cleanser. According to various aspects also provided herein, a composition includes: (i) an aqueous solvent; (ii) benzyl alcohol; (iii) ethylhexylglycerin; and (iv) at least one saturated non-ionic ethoxylated fatty acid ester. The resulting composition is suitable for application to the skin of a subject for cleansing the skin.

As described above, Septisol® is commonly used as an emulsifier for deep chemical peels because of past availability in clinics and hospitals, as a common hand-wash antibacterial soap (due to the presence of hexachlorophene, which was later replaced by triclosan). However, chemical peels incorporating Septisol® begin separating into two distinct phases in about 90 seconds and become fully separated in about 15 minutes. As a result, surgeons tasked with applying chemical peels incorporating Septisol® must frequently swirl these mixtures in a cup. If the surgeon is not constantly monitoring to the state of uniformity of the emulsion, such as by using an opaque or metal cup, the surgeon may dip his applicator in random areas of the two phases. Such an ad hoc procedure may lead to the application of non-uniform concentrations of these abrasive peels to various areas of a subject's skin and may create highly disparate results within and between subjects. Moreover, Septisol® was discontinued on Jan. 1, 2019, thereby creating a need for alternative emulsifiers. Contrary to prior compositions and methods, various aspects provided herein have a rate of separation of less than or equal to 0.5 mm/s, which correlates to a substantially fully emulsified mixture for at least about 120 minutes, the usual duration of a full-face chemical peel procedure.

It was unexpectedly discovered that alternative emulsifiers that incorporate at least one saturated non-ionic ethoxylated fatty acid ester are suitable for use in a chemical peel composition. It was more unexpectedly discovered that chemical peel incorporating these one saturated non-ionic ethoxylated fatty acid ester are stable for hours and provide comparable results to typical chemical peels, thereby allowing both significant efficacy and enhanced homogeneity when applied to the skin. Illustrative examples of conventional deep peels formulated according to Hetter's specifications, including the rapid phase separation of such formulations and the different skin effects resulting from the formation of upper and lower phases may be found in Justo, CARACTERIZAÇÃO QUÍMICA ÓLEO DE Croton tiglium (EUPHORBIACEAE) E AVALIAÇÃO DO PERFIL DERMATOLÓGICO DO PEELING DE FENOL COM ÓLEO DE CROTON, UNIVERSIDADE ESTADUAL DE PONTA GROSSA (2018).

As described above, in various aspects, a composition for treating skin conditions may include: (i) an aqueous solvent; (ii) phenol; (iii) croton oil; and (iv) at least one saturated non-ionic ethoxylated fatty acid ester. The composition has a separation rate of less than or equal to 0.5 mm/s, less than or equal to 0.2 mm/s, less than or equal to 10 mm/min; less than or equal to 5 mm/min, less than or equal to 1 mm/min, less than or equal to 10 mm/hr, less than or equal to 5 mm/hr, or less than or equal to 1 mm/hr.

In aspects, the aqueous solvent is present in the composition at a concentration from 50% by weight to 99% by weight. In other aspects, the aqueous solvent is present in the composition at a concentration from 55% by weight to 99% by weight, from 60% by weight to 99% by weight, from 65% by weight to 99% by weight, from 75% by weight to 99% by weight, from 80% by weight to 99% by weight, from 85% by weight to 99% by weight, from 90% by weight to 99% by weight, from 50% by weight to 95% by weight, from 60% by weight to 95% by weight, from 70% by weight to 95% by weight, from 80% by weight to 95% by weight, or from 90% by weight to 95% by weight. It is specifically appreciated that any value or range from 50% by weight to 99% by weight of aqueous solution is envisioned as part of the disclosure. The aqueous solvent, according to aspects, includes water. The aqueous solvent in some aspects is water alone and excludes other aqueous or non-aqueous solvents.

Phenol is present in the composition, according to aspects, at a concentration of from 5% by weight to 90% by weight, or from 5% by weight to 50% by weight. In other aspects, the phenol is present in the composition at a concentration from 10% by weight to 80% by weight, from 15% by weight to 70% by weight, from 20% by weight to 60% by weight, from 25% by weight to 50% by weight, or from 30% by weight to 40% by weight. In other aspects, the phenol is present in the composition at a concentration from 10% by weight to 50% by weight, from 15% by weight to 50% by weight, from 20% by weight to 50% by weight, from 25% by weight to 50% by weight, or from 30% by weight to 50% by weight, from 10% by weight to 40% by weight, from 15% by weight to 40% by weight, from 20% by weight to 40% by weight, from 25% by weight to 40% by weight, or from 30% by weight to 40% by weight, from 10% by weight to 30% by weight, from 15% by weight to 30% by weight, from 20% by weight to 30% by weight, or from 25% by weight to 30% by weight. It is specifically appreciated that any value or range from 5% by weight to 90% by weight or from 5% by weight to 50% by weight of the phenol is envisioned as part of the disclosure.

In aspects, croton oil is present in the composition at a concentration from 0.0001% by weight to 3.0% by weight. In other aspects, the croton oil is present in the composition at a concentration from 0.001% by weight to 2.8% by weight, from 0.01% by weight to 2.6% by weight, from 0.1% by weight to 2.4% by weight, from 0.5% by weight to 2.2% by weight, from 1.0% by weight to 2.0% by weight, from 1.2% by weight to 1.8% by weight, or from 1.5% by weight to 1.7% by weight. It is specifically appreciated that any value or range from 0.0001% by weight to 3.0% by weight of the croton oil is envisioned as part of the disclosure.

Moreover, in various aspects, at least one saturated non-ionic ethoxylated fatty acid ester is present in the composition at a concentration from 0.1% by weight to 1.0% by weight. For example, the at least one saturated non-ionic ethoxylated fatty acid ester may be present in the composition at a concentration from 0.1% by weight to 0.9% by weight, from 0.2% by weight to 0.8% by weight, from 0.25% by weight to 0.75% by weight, from 0.3% by weight to 0.7% by weight, from 0.3% by weight to 0.6% by weight, from 0.35% by weight to 0.5% by weight, or from 0.35% by weight to 0.45% by weight. In aspects, the at least one saturated non-ionic ethoxylated fatty acid ester is present in the composition at a concentration of less than 1.0% by weight, less than 0.9% by weight, less than 0.8% by weight, less than 0.7% by weight, less than 0.6% by weight, or less than 0.5% by weight. It is specifically appreciated that any value or range from 0.1% by weight to 1.0% by weight of the at least one saturated non-ionic ethoxylated fatty acid ester is envisioned as part of the disclosure. Without wishing to be bound by theory, it is believed that stability of the composition dramatically declines when the at least one saturated non-ionic ethoxylated fatty acid ester is incorporated into composition outside of the described range. A composition optionally excludes texachlorophene, triclosan, or both.

The at least one saturated non-ionic ethoxylated fatty acid ester, according to some aspects, includes a substituted or unsubstituted alkyl, alkenyl, alkynyl carbon chain length from 8 carbon atoms to 18 carbon atoms, optionally 8 to 12 carbon atoms. The carbon chain is optionally linear or branched. Optionally, the carbon chain is not cyclic. In various aspects, the carbon chain of the at least one saturated non-ionic ethoxylated fatty acid ester is a saturated carbon chain.

In aspects, the at least one saturated non-ionic ethoxylated fatty acid ester has a hydrophile-lipophile balance (HLB) value of greater than or equal to 15.0. In other aspects, the at least one saturated non-ionic ethoxylated fatty acid ester has a HLB value of greater than or equal to 15.1, 15.2, 15.3, 15.4, 15.5, 15.6, 15.7, 15.8, 15.9, 16.0, 16.1, 16.2, 16.3, 16.4, 16.5, or 16.6. In additional aspects, the at least one saturated non-ionic ethoxylated fatty acid ester has a HLB value from 16.5 to 19.5. Without being bound by theory, the term "HLB" is used an empirical expression for the relationship of the hydrophilic and hydrophobic groups of an emulsifier.

In aspects, the at least one at least saturated one non-ionic ethoxylated fatty acid ester comprises a polyethylene glycol sorbitan laurate. Suitable polyethylene glycol sorbitan laurates may include, by way of example and not limitation, polyethylene glycol 20 (PEG-20) sorbitan monolaurate, polyethylene glycol 80 (PEG-80) sorbitan laurate, and combinations thereof. Illustrative examples PEG-20 include Tween® 20, sold by Sigma-Aldrich®. Illustrative examples of PEG-80 include Tween® 28, sold by Croda Inc.

In some aspects, benzyl alcohol is present in the composition. In such aspects, the benzyl alcohol may be present at a concentration from 0.5% by weight to 1.5% by weight. Without being bound by theory, it is believed that the benzyl alcohol functions as a preservative in the composition, particularly when in combination with ethylhexylglycerin. Moreover, benzyl alcohol is typically well-tolerated for dermatological applications and is volatile, and, thus, some of the benzyl alcohol evaporates on application to the skin, further reducing the possibility of it interacting (and particularly, adversely interacting) with the peel action. In aspects, the benzyl alcohol is present in the composition at a concentration from 0.6% by weight to 1.4% by weight, from 0.7% by weight to 1.3% by weight, from 0.75% by weight to 1.25% by weight, from 0.8% by weight to 1.2% by weight, from 0.9% by weight to 1.2% by weight, or from 1.0% by weight to 1.2% by weight. It is specifically appreciated that any value or range from 0.5% by weight to 1.5% by weight benzyl alcohol is envisioned as part of the disclosure.

In some aspects, the composition further includes ethylhexylglycerin. When included, the ethylhexylglycerin is present in the composition at a concentration from 0.01% by weight to 0.50% by weight. Without being bound by theory, it is believed that the ethylhexylglycerin functions as a preservative in the composition. In aspects, the ethylhexylglycerin is present in the composition at a concentration from 0.02% by weight to 0.45% by weight, from 0.03% by weight to 0.40% by weight, from 0.04% by weight to 0.35% by weight, from 0.05% by weight to 0.30% by weight, from 0.06% by weight to 0.25% by weight, from 0.07% by weight to 0.20% by weight, from 0.08% by weight to 0.15% by weight, or from 0.09% by weight to 0.11% by weight. It is specifically appreciated that any value or range from 0.01% by weight to 0.50% by weight the ethylhexylglycerin is envisioned as part of the disclosure.

According to various aspects, the composition is free of triclosan and/or hexachlorophene. In some aspects, the composition is free of components other than those explicitly recited herein as included in an exemplary composition. Accordingly, in some aspects, the composition "consists of" or "consists essentially of" the aqueous solvent, phenol, croton oil, and one or more saturated non-ionic ethoxylated fatty acid ester, and optionally benzyl alcohol, ethylhexylglycerin, a pH adjuster, a fragrance, a color, or any selection therefrom. In aspects, the composition consists essentially of from 50% by weight to 99% by weight water, from 30% by weight to 40% by weight phenol, from 1.0% by weight to 2.0% by weight croton oil, and from 0.1% by weight to 1.0% by weight PEG-80 sorbitan laurate.

According to various aspects, the composition is free of triclosan and/or hexachlorophene, phenol and croton oil and can be used as a cleanser instead of as a chemical peel. Accordingly, in some aspects, the composition "consists of" or "consists essentially of" the aqueous solvent, benzyl alcohol, ethylhexylglycerin, and one or more saturated non-ionic ethoxylated fatty acid ester, and optionally a pH adjuster, a fragrance, a color, or any selection therefrom.

The composition, according to aspects, may be provided in any suitable form of delivery. In certain aspects, the composition is provided in a form selected from the group consisting of a lotion, a cream, a gel, an ointment, a suspension, and a liquid. In one or more of such aspects, a thickener may be included, such as to generate a cream or gel.

Other additives are contemplated depending on the particular aspects. For example, some aspects may include, by way of example and not limitation, pH adjusters, colorants, and fragrances. In various aspects, any such components are preferably dermatologically acceptable and do not interfere with the efficacy or impose any negative influence upon the efficacy of the composition.

Suitable pH adjusters can include, for example, acids, bases, buffers, and any other known pH adjusters or modifiers useful in cosmetic formulations are known. See, e.g. International Cosmetic Ingredient Dictionary and Handbook ($9^{th}$ ed. 2002, and subsequent editions). Non-limiting examples of pH adjusters suitable for use in various aspects include acetic acid, ascorbic acid, citric acid, sodium citrate, tartaric acid, ammonium hydroxide, and mixtures thereof. When present, the pH adjuster is present in an amount such as to result in a final pH of the composition of from about 5 to about 6, or from about 5 to about 5.75, or from about 5 to about 5.5, including all ranges and sub ranges therebetween. In aspects, the pH adjuster is present in an amount such as to result in a pH of the composition prior to the addition of phenol of from about 10 to about 11, including all ranges and sub ranges therebetween.

One or more colorants may be included in some aspects. Suitable colorants can be chosen from pigments, dyes, such as liposoluble dyes, nacreous pigments, and pearling agents. Representative liposoluble dyes can include Sudan Red, DC Red 17, DC Green 6, β-carotene, soybean oil, Sudan Brown, DC Yellow 11, DC Violet 2, DC Orange 5, annatto, and quinoline yellow. Suitable nacreous pigments which may be used may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. Example pigments which may be used may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

A composition optionally includes one or more additives. It is appreciated, however, that a composition is optionally free of an additive. An additive illustratively is one or more antioxidants, anti-static agents, buffering agents, bulking agents, chelating agents, cleansers, colorants, conditioners, deodorants, diluents, dyes, emollients, flavonoids, fragrances, hair conditioners, humectants, ionization agents, moisturizers, occlusive agents, perfuming agents, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. The source and type of additive operable herein is readily understood by one of skill in the art. Illustrative examples of additives are found in WO 2009/090558 and references cited therein each of which are incorporated herein by reference.

According to some aspects, the composition may include an internal phase that includes the phenol and the croton oil. In such aspects, the internal phase has a uniform or substantially uniform particle size from 1 micron to 2 microns. For example, the particle size may be greater than or equal to 1 micron and less than or equal to 2 microns, greater than or equal to 1 micron and less than or equal to 1.8 microns, greater than or equal to 1 micron and less than or equal to 1.6 microns, greater than or equal to 1 micron and less than or equal to 1.4 microns, or greater than or equal to 1 micron and less than or equal to 1.2 microns.

In certain aspects, the composition has a separation rate of less than or equal to 0.5 mm/s, less than or equal to 0.2 mm/s, less than or equal to 10 mm/min; less than or equal to 5 mm/min, less than or equal to 1 mm/min, less than or equal to 10 mm/hr, less than or equal to 5 mm/hr, or less than or equal to 1 mm/hr. Separation rate may be measured at 25° C. and 1 atm.

In some particular aspects, the composition for treating skin conditions includes or is exclusively (i) from 50% by weight to 99% by weight water, (ii) from 30% by weight to 40% by weight phenol, (iii) from 1.0% by weight to 2.0% by weight croton oil, and (iv) from 0.1% by weight to 1.0% by weight PEG-80 sorbitan laurate. The composition has a rate of separation of less than or equal to 0.5 mm/s, and is substantially in the form of an emulsion for greater than or equal to 120 minutes.

Any of the compositions described in this section may be incorporated into methods for treating skin conditions. In aspects, the method comprises topically applying a material formed from or being the composition of various aspects to skin of a subject. In particular, the composition may be wiped onto the skin until clinical signs appear, such as frosting. As described hereinabove, the chemical peel may be formed from a composition comprising (i) an aqueous solvent, (ii) phenol, (iii) croton oil, and (iv) at least one saturated non-ionic ethoxylated fatty acid ester. The skin may include the epidermis, papillary dermis, upper reticular dermis, or combinations thereof.

As described above, various aspects provide compositions suitable for cleansing skin. In particular, it was discovered that the vehicle of aspects described above, without incorporating phenol and croton, produce a mild skin cleansing agent. Various preservatives may be added to the skin cleansing agent, which can then be packaged, offered, and sold as a standalone product. Accordingly, in various aspects, a composition for cleansing skin comprises (i) an aqueous solvent, (ii) benzyl alcohol, (iii) ethylhexylglycerin, and (iv) at least one saturated non-ionic ethoxylated fatty acid ester.

In aspects, the aqueous solvent is present in the composition at a concentration from 90% by weight to 99% by weight. In other aspects, the aqueous solvent is present in the composition at a concentration from 91% by weight to 99% by weight, from 92% by weight to 99% by weight, from 93% by weight to 99% by weight, from 94% by weight to 99% by weight, from 95% by weight to 99% by weight, from 96% by weight to 99% by weight, or from 97% by weight to 99% by weight. It is specifically appreciated that any value or range from 90% by weight to 99% by weight of aqueous solution is envisioned as part of the disclosure. The aqueous solvent, according to aspects, includes water.

Benzyl alcohol is present in the composition, according to various aspects, at a concentration from 0.5% by weight to 1.5% by weight. Without being bound by theory, it is believed that the benzyl alcohol functions as a preservative in the composition. In aspects, the benzyl alcohol is present in the composition at a concentration from 0.6% by weight to 1.4% by weight, from 0.7% by weight to 1.3% by weight, from 0.75% by weight to 1.25% by weight, from 0.8% by weight to 1.2% by weight, from 0.9% by weight to 1.2% by weight, or from 1.0% by weight to 1.2% by weight. It is specifically appreciated that any value or range from 0.5% by weight to 1.5% by weight benzyl alcohol is envisioned as part of the disclosure.

In various aspects, ethylhexylglycerin is present in the composition at a concentration from 0.01% by weight to 0.50% by weight. Without being bound by theory, it is believed that the ethylhexylglycerin functions as a preservative in the composition. In aspects, the ethylhexylglycerin is present in the composition at a concentration from 0.02% by weight to 0.45% by weight, from 0.03% by weight to 0.40% by weight, from 0.04% by weight to 0.35% by weight, from 0.05% by weight to 0.30% by weight, from 0.06% by weight to 0.25% by weight, from 0.07% by weight to 0.20% by weight, from 0.08% by weight to 0.15% by weight, or from 0.09% by weight to 0.11% by weight. It is specifically appreciated that any value or range from 0.01% by weight to 0.50% by weight the ethylhexylglycerin is envisioned as part of the disclosure.

According to various aspects, at least one saturated non-ionic ethoxylated fatty acid ester is present in the composition at a concentration from 0.1% by weight to 1.0% by weight. For example, the at least one saturated non-ionic ethoxylated fatty acid ester may be present in the composition at a concentration from 0.1% by weight to 0.9% by weight, from 0.2% by weight to 0.8% by weight, from 0.25% by weight to 0.75% by weight, from 0.3% by weight to 0.7% by weight, from 0.3% by weight to 0.6% by weight, from 0.35% by weight to 0.5% by weight, or from 0.35% by weight to 0.45% by weight. In aspects, the at least one saturated non-ionic ethoxylated fatty acid ester is present in the composition at a concentration of less than or equal to 1.0% by weight, less than or equal to 0.9% by weight, less than or equal to 0.8% by weight, less than or equal to 0.7% by weight, less than or equal to 0.6% by weight, or less than or equal to 0.5% by weight. It is specifically appreciated that any value or range from 0.1% by weight to 1.0% by weight of the at least one saturated non-ionic ethoxylated fatty acid ester is envisioned as part of the disclosure. Without wishing to be bound by theory, it is believed that stability of the composition dramatically declines when the at least one saturated non-ionic ethoxylated fatty acid ester is incorporated into composition outside of the described range.

The at least one saturated non-ionic ethoxylated fatty acid ester, according to various aspects, includes a carbon chain length from 8 carbon atoms to 12 carbon atoms. In certain aspects, the carbon chain of the at least one saturated non-ionic ethoxylated fatty acid ester is a saturated carbon chain.

According to various aspects, the at least one saturated non-ionic ethoxylated fatty acid ester has a hydrophile-lipophile balance (HLB) value of greater than or equal to 15.0. For example, the at least one saturated non-ionic ethoxylated fatty acid ester may have a HLB value of greater than or equal to 15.1, 15.2, 15.3, 15.4, 15.5, 15.6, 15.7, 15.8, 15.9, 16.0, 16.1, 16.2, 16.3, 16.4, 16.5, or 16.6. In aspects, the at least one saturated non-ionic ethoxylated fatty acid ester has a HLB value from 16.5 to 19.5. Without being bound by theory, the term "HLB" is used an empirical expression for the relationship of the hydrophilic and hydrophobic groups of an emulsifier.

In aspects, the at least one at least saturated one non-ionic ethoxylated fatty acid ester comprises a polyethylene glycol sorbitan laurate. Suitable polyethylene glycol sorbitan laurates include, by way of example and not limitation, polyethylene glycol 20 (PEG-20) sorbitan monolaurate, polyethylene glycol 80 (PEG-80) sorbitan laurate, and combinations thereof. Illustrative examples PEG-20 include Tween® 20, sold by Sigma-Aldrich®. Illustrative examples of PEG-80 include Tween® 28, sold by Croda Inc.

A composition may be provided as a lotion, cream, gel, bar, ointment, suspension, liquid, or impregnated pad, optionally where a liquid is supplied separately from a pad but applied thereto prior to application to the skin. In some aspects, thickeners or other additives may be added to the composition, such as may be needed to achieve a desired form of the composition. In some aspects, the composition is provided in a single use container, the contents of which are applied directly to the skin of a subject or applied to an applicator pad for subsequent delivery to the subject.

In one particular aspect, the composition for treating skin conditions includes (i) from 90% by weight to 99% by weight water, (ii) from 0.5% by weight to 1.5% by weight benzyl alcohol, (iii) from 0.01% by weight to 0.5% by weight ethylhexylglycerin, and (iv) from 0.1% by weight to 1.0% by weight PEG-80 sorbitan laurate.

According to various aspects, the composition is free of triclosan. In some aspects, the composition is free of other components. Accordingly, in some aspects, the composition "consists of" or "consists essentially of" the aqueous solvent, benzyl alcohol, ethylhexylglycerin, and one or more saturated non-ionic ethoxylated fatty acid ester. In aspects, the composition consists essentially of from 90% by weight to 99% by weight water, from 0.5% by weight to 1.5% by weight benzyl alcohol, from 0.01% by weight to 0.5% by weight ethylhexylglycerin, and from 0.1% by weight to 1.0% by weight PEG-80 sorbitan laurate.

Any of the compositions described in this section may be incorporated into methods for cleansing skin. In aspects, the method comprises topically applying a skin cleansing agent formed from the composition of various aspects to skin of a subject. As described hereinabove, the cleansing agent may be formed from a composition comprising (i) an aqueous solvent, (ii) benzyl alcohol, (iii) ethylhexylglycerin, and (iv) at least one saturated non-ionic ethoxylated fatty acid ester. The skin may include the epidermis, papillary dermis, upper reticular dermis, or combinations thereof.

EXAMPLES

Various aspects of the present invention are illustrated by the following non-limiting examples. The examples are for illustrative purposes and are not a limitation on any practice of the present invention. It will be understood that variations and modifications can be made without departing from the spirit and scope of the disclosure. Reagents used are known to those of skill in the art who understand from which sources such agents may be obtained or how such reagents are synthesized from commercially available materials.

The following examples are given by way of illustration and are in no way intended to limit the scope of the present invention.

Example 1

A conventional skin peel composition, including Septisol®, according to Hetter's formula was prepared. This conventional composition (CE1) included 61% by weight distilled water, 33% by weight phenol, 4.6% by weight hexachlorophene (Septisol®), and 1.4% by weight croton oil. It was prepared by mixing together 6 mL of the distilled water, 4 mL of the phenol, 16 drops of Septisol®, and 2 drops of croton oil in a vial. The vial was then agitated (i.e., shaken) for 15-30 seconds to create CE1.

Additionally, a skin peel composition according to aspects described herein was prepared. This inventive composition (IE1) included 63% by weight distilled water, 35% by weight phenol, 1.6% by weight croton oil, and 0.4% by weight Tween® 28, sold by Croda Inc. The composition was prepared by mixing together all of the components in a vial. The vial was then agitated (i.e., shaken) for 15-30 seconds to create TE1.

As can be seen in FIG. 1, the components of CE1 began separating into two distinct phases almost immediately following the conclusion of agitation. Within 90 seconds of agitation, a slightly yellow bottom layer comprising the phenol and croton oil separated from the gray, hazy top layer comprising Septisol® and water. This separation was nearly heterogeneous within three minutes of agitation and was completely heterogeneous by 17 minutes after agitation of the vial.

These results indicate that the conventional skin peels incorporating Septisol® must be continuously agitated so as to maintain any semblance of homogeneity. However, this constant agitation (a) is very difficult to maintain while applying the skin peel to a single subject and (b) varies dramatically between surgeons tasked with maintaining homogeneity when applying the typical skin peels. Even if the composition is continuously agitated, separation may occur on the applicator itself, which may lead to inconsistent results in different areas of the contacted skin.

Therefore, the quality of the skin peel may vary dramatically from patient to patient, and even between application locations on a single patient since the phase separation of conventional skin peels that include Septisol®, such as CE1, begin almost immediately.

Figure 2:
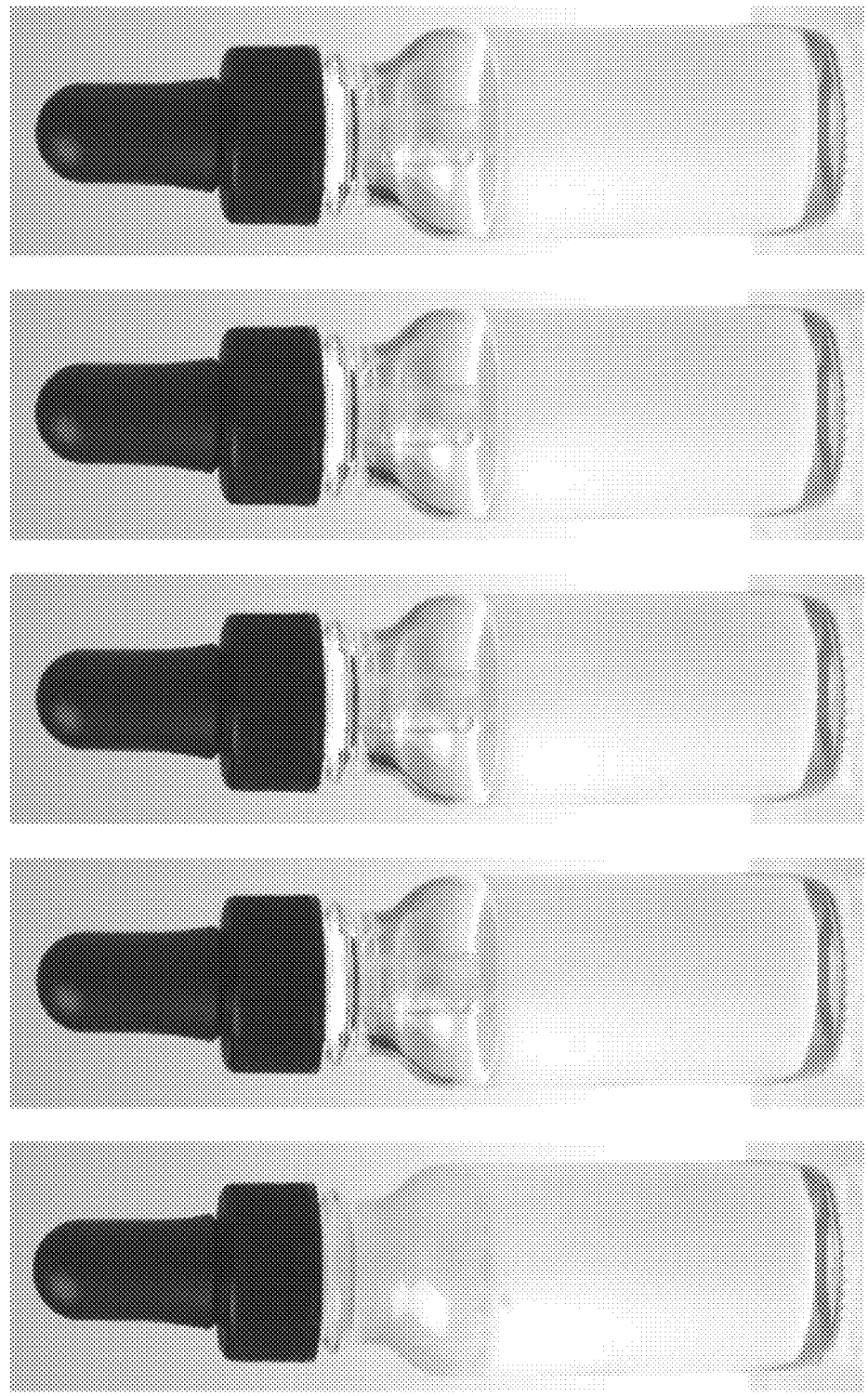
FIG. 2 illustrates the homogeneity of the composition according to an aspect of a skin peel composition as provided herein.

However, as can be seen in FIG. 2, the components of IE1 maintained homogeneity for at least 120 minutes. Without being bound by theory, it is believed that this homogeneity is due to the formation of an internal phase, which includes the phenol and the croton oil, having a uniform particle size of from 1 micron to 2 microns. The Tween® 28, acting as an emulsifier, enabled the internal phase to stay uniformly dispersed throughout IE1.

Such long-lasting homogeneity can ensure that those responsible for applying the composition (i.e., surgeons) will not have to constantly agitate it to maintain the composition's homogeneity. As such, the homogeneity achieved in IE1 represents maintained dispersion between patients and during the same procedure. As a result, the surgeon will no longer be forced to simultaneously agitate and apply the composition as the IE1 skin peel remained in a single phase throughout the entirety of the procedure.

Moreover, when IE1 was used as a skin peel composition, the subject had a more consistent response to its application than CE1, as the frosting (which indicates proper application) took the same time to appear in all contacted areas. In contrast, skin peels incorporating CE1 often need reapplication with different amounts of friction, pressure, and volume, which may lead to even more inconsistent results. Therefore, skin peels incorporating IE1 provide a wide ranging variety of benefits over CE1 including (a) more consistent application; (b) more consistent results; (c) increased homogeneity of the skin peel; (d) no phase separation on the applicator; and (e) easier application by the surgeon to the subject.

Example 2

A skin cleansing agent incorporating Tween® 28, sold by Croda Inc., but without the internal phase described above, was also prepared. In particular, this inventive composition (IE2) included 98.1% by weight distilled water, 1.1% by weight benzyl alcohol, 0.7% by weight Tween® 28, sold by Croda Inc., and 0.1% by weight ethylhexylglycerin. This composition was prepared by mixing together all of the components in a vial. The vial was then agitated (i.e., shaken) for 15-30 seconds to create IE2.

It was discovered in IE2 that the benzyl alcohol and the ethylhexylglycerin both functioned as preservatives that allow the composition to maintain its homogeneity for days, weeks, months, or even years. Moreover, it was unexpectedly discovered that Tween® 28 was able to function as a skin cleansing agent in IE2, even without the incorporation of phenol and/or croton oil. As such, it is contemplated that IE2 may be used by subjects as a mild skin cleansing agent.

Example 3

To better understand the differences of effect between comparative and inventive formulae, microscopic depth of injury was evaluated in biopsies performed at the first post-operative day after the application of comparative example 2 (CE2) or inventive example 3 (IE3).

CE2 included 1.6% by weight croton oil, 35% by weight phenol, and 5% by weight Septisol® in water. IE3 included 1.6% by weight croton oil, 35% by weight phenol, and 5% Novisol (PEG-80 sorbitan laurate) in water. The compositions were prepared by mixing together all of the components for each composition in a corresponding vial. The vials were then agitated (i.e., shaken) for 15-30 seconds to create CE2 and IE3.

Figure 3:
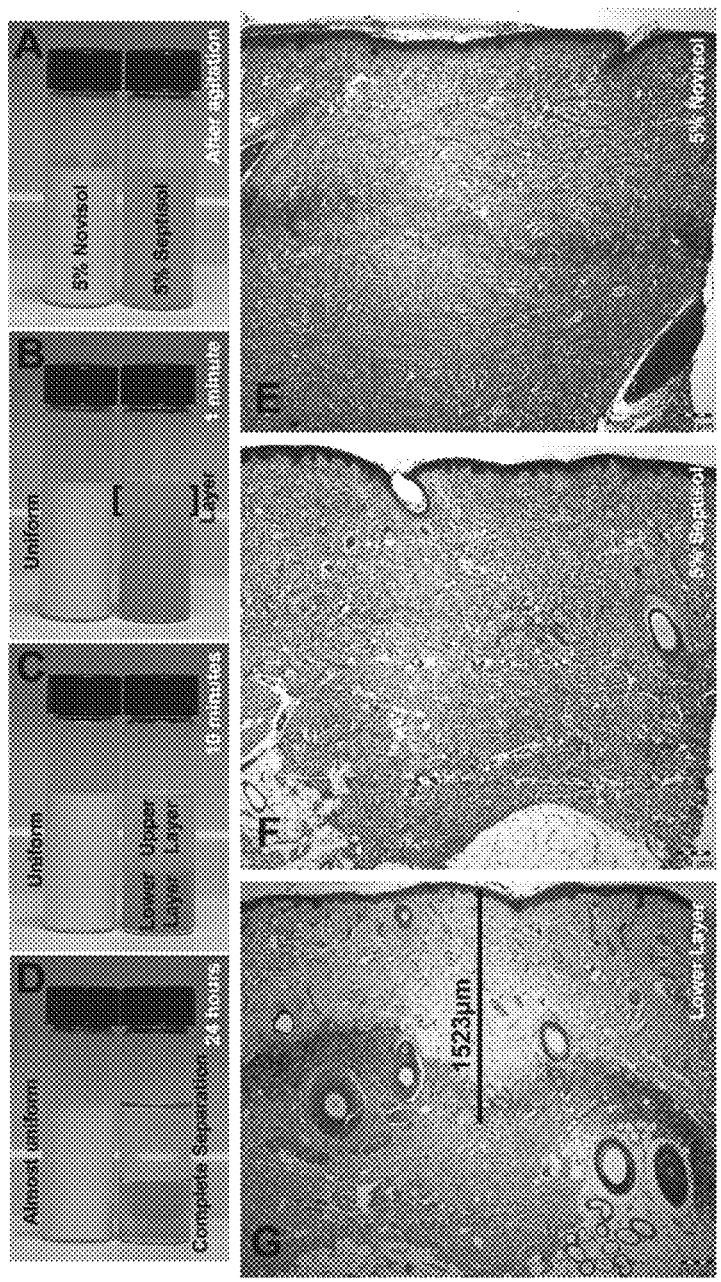
FIG. 3A illustrates a composition according to an aspect disclosed herein (left) and a conventional composition (right) immediately after agitation.
FIG. 3B illustrates a composition according to an aspect disclosed herein (left) and a conventional composition (right) after settling for one minute.
FIG. 3C illustrates a composition according to an aspect disclosed herein (left) and a conventional composition (right) after settling for ten minutes.
FIG. 3D illustrates a composition according to an aspect disclosed herein (left) and a conventional composition (right) after settling for 24 hours.
FIG. 3E is an image of a section of porcine skin stained with hematoxylin and eosin at 40× magnification 24 hours post-treatment with a composition according to an aspect disclosed herein.
FIG. 3F is an image of a section of porcine skin stained with hematoxylin and eosin at 40× magnification 24 hours post-treatment with a conventional composition immediately after agitation.
FIG. 3G is an image of a section of porcine skin stained with hematoxylin and eosin at 40× magnification 24 hours post-treatment with the lower layer of a conventional composition after settling for 10 minutes.

As seen in FIG. 3A, immediately after agitation, both CE2 (right) and IE3 (left) were substantially homogeneous, with IE3 forming a milky emulsion and CE2 forming an orange-colored formula. After one minute, however, CE2 (right) began to separate into layers with a white layer on the top (indicated in brackets), while IE3 (left) remained homogeneous, as shown in FIG. 3B. After ten minutes, CE2 (right) distinctly formed two cloudy layers: an upper layer and a lower layer, while IE3 (left) was homogeneous (FIG. 3C). After 24 hours, CE2 (right) had completely separated into a clear upper layer and an orange lower layer while IE3 (left) was nearly uniform (FIG. 3D).

Next, IE3 and CE2 were used to treat porcine skin. Specifically, CE2 was used immediately after agitation as one treatment and the lower layer isolated from CE2 after 10 minutes was used as another treatment. FIGS. 3E (IE3), 3F (CE2 immediately after agitation), and 3G (CE2 lower layer after 10 minutes) show sections of 24 hour post-peel biopsies taken from the center of 2 cm×2 cm spots of porcine skin treated with each formula and stained with hematoxylin and eosin at 40× magnification. The depth of injury was measured from the top of the epidermis to the deepest level of the peri-coagulative inflammatory band, which is indicated by the arrow in FIG. 3G.

To measure the depth of injury, four sections for each formula were analyzed independently by two unblinded evaluators using ImageJ v. 1.51j8 software (National Institutes of Health, MD) to measure from the top of the epidermis to the deepest level of the peri-coagulative necrosis inflammatory band. Ten measurements were taken for each section by each evaluator. All measurements were combined for analysis of the distribution of the depth of injury for each formula. The results are shown in FIG. 4.

In particular, the measurements for CE2 immediately after agitation had a median of 922 μm, with an interquartile range of 610 μm and a maximum depth of injury of 1475 μm. The measurements for the lower layer of CE2 after 10 minutes had a median of 1280 μm, with an interquartile range of 429 μm and a maximum depth of injury of 2642 μm. In contrast, the measurements for IE3 had a median of 1188 μm, with an interquartile range of 483 μm and a maximum depth of injury of 1592 μm. All of the plots demonstrate bimodal distribution with one curve close to the target depth for a very heavy deep chemical peel, which ranges from approximately 800 μm to approximately 1600 μm, corresponding to mid- to deep-reticular dermis. Areas with a measured depth of injury of less than 500 μm represented the typical depth of medium-depth chemical peels, with injury past the papillary dermis, but not fully reaching the reticular dermis. The lower layer formula presented areas of full-thickness dermal necrosis when greater than 2000 μm, and is, therefore, not recommended as a safe chemical peel due to the possibility of scar formation.

Figure 4:
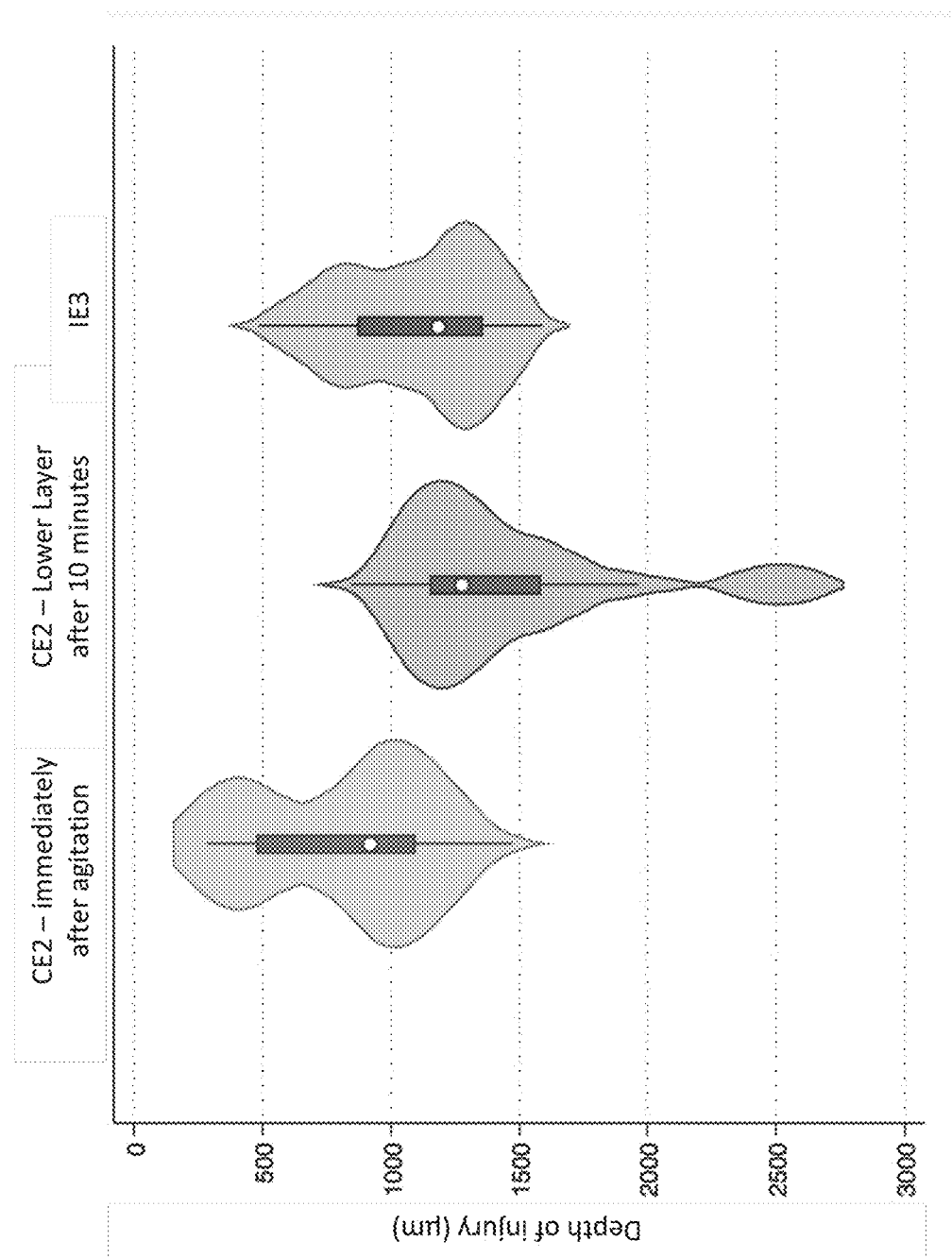
FIG. 4 is a violin plot showing the density of the depth of injury measurements (in μm) for a conventional composition immediately after agitation, the lower layer of a conventional composition after settling for 10 minutes, and a composition according to an aspect disclosed herein.

As shown in FIG. 4, when the layers are mixed into an unstable emulsion (CE2 immediately after agitation), there is greater variation in depth of injury as compared to the use of a more stable emulsion (IE3). When the formula of CE2 was allowed to separate for 10 minutes, the upper layer presented no relevant histologic effects, and the lower layer was shown to be the active layer, concentrating the phenol and active chemicals of croton oil, which includes multiple cytotoxic phorbol esters. Accordingly, with insufficient agitation, the depth of injury can vary between no damage when the upper layer is applied to very deep (e.g., greater than 2600 μm) damage when the lower layer is applied.

These results suggest that the stability of the emulsion is important for both safety and efficacy of the composition. In particular, without stability, a cotton-tipped applicator can absorb more concentrated emulsion zones, which can lead to complications such as scarring. Improved stability can provide more predictable, uniform effects and reduce the need for constant agitation of the formula.

It is appreciated that all reagents are obtainable by sources known in the art unless otherwise specified.

The foregoing description of particular aspect(s) is merely exemplary in nature and is in no way intended to limit the scope of the disclosure, its application, or uses, which may, of course, vary. The disclosure is presented with relation to the non-limiting definitions and terminology included herein. These definitions and terminology are not designed to function as a limitation on the scope or practice of the disclosure but are presented for illustrative and descriptive purposes only. While the processes and devices are described as an order of individual steps or using specific arrangements of elements, it is appreciated that described steps or elements may be interchangeable such that the description includes multiple parts or steps arranged in many ways as is readily appreciated by one of skill in the art.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Patents and publications mentioned in the specification are indicative of the levels of those skilled in the art to which the invention pertains. Each patent, application or publication is incorporated herein by reference to the same extent as if each individual patent, application or publication was specifically and individually stated as incorporated herein by reference for the specific teaching for with each reference is cited and additionally for entirety of their contents including text, figures, and references. Citation of any document is not to be construed as an admission that it is prior art with respect to the present invention.

The foregoing description is illustrative of particular aspects of the invention, but is not meant to be a limitation upon the practice thereof.

The invention claimed is:

1. A composition for treating a skin condition, comprising consisting of:
    (i) an aqueous solvent;
    (ii) phenol;
    (iii) from 0.0001% by weight to 3.0% by weight croton oil;
    (iv) at least one saturated non-ionic ethoxylated fatty acid ester;
    (v) at least one pH adjuster; and
    (vi) at least one preservative,
    wherein the composition has a rate of separation of less than or equal to 0.5 mm/s.

2. The composition according to claim 1, wherein the aqueous solvent is present in the composition at a concentration from 50% by weight to 99% by weight.

3. The composition according to claim 2, wherein the phenol is present in the composition at a concentration from 5% by weight to 90% by weight.

4. The composition according to claim 3, wherein the croton oil is present in the composition at a concentration from 0.1% by weight to 2.0% by weight.

5. The composition according to claim 4, wherein the at least one saturated non-ionic ethoxylated fatty acid ester is present in the composition at a concentration from 0.1% by weight to 1.0% by weight.

6. The composition according to claim 1, wherein the phenol is present in the composition at a concentration from 5% by weight to 90% by weight.

7. The composition according to claim 1, wherein the at least one saturated non-ionic ethoxylated fatty acid ester is present in the composition at a concentration from 0.1% by weight to 1.0% by weight.

8. The composition according to claim 1, wherein the at least one saturated non-ionic ethoxylated fatty acid ester is present in the composition at a concentration of less than 0.5% by weight.

9. The composition according to claim 1, wherein the at least one saturated non-ionic ethoxylated fatty acid ester comprises a carbon chain length from 8 carbon atoms to 12 carbon atoms.

10. The composition according to claim 1, wherein the at least one saturated non-ionic ethoxylated fatty acid ester has a hydrophile-lipophile balance (HLB) value of greater than or equal to 15.0.

11. The composition according to claim 1, wherein the at least one at least saturated one non-ionic ethoxylated fatty acid ester comprises a polyethylene glycol sorbitan laurate.

12. The composition according to claim 11, wherein the polyethylene glycol sorbitan laurate is selected from the group consisting of PEG-20 sorbitan monolaurate, PEG-80 sorbitan laurate, and combinations thereof.

13. The composition according to claim 1, wherein the composition is provided in a form selected from the group consisting of a lotion, a cream, a gel, an ointment, a suspension, and a liquid.

14. The composition according to claim 1, further comprising an internal phase consisting of the phenol and the croton oil.

15. The composition according to claim 14, wherein the internal phase comprises a uniform particle size from 1 micron to 2 microns.

16. The composition according to claim 1, wherein the composition is free of triclosan.

17. The composition according to claim 1, wherein the aqueous solvent comprises water.

18. A composition for treating a skin condition, consisting of:
    (i) from 50% by weight to 99% by weight water;
    (ii) from 30% by weight to 40% by weight phenol;
    (iii) from 1.0% by weight to 2.0% by weight croton oil;
    (iv) from 0.1% by weight to 1.0% by weight PEG-80 sorbitan laurate;
    (v) from 0.5% by weight to 1.5% by weight benzyl alcohol, and/or from 0.01% by weight to 0.50% by weight ethylhexylglycerin; and
    (vi) at least one pH adjuster,
    wherein the composition has a rate of separation of less than or equal to 0.5 mm/s.

19. A method for treating wrinkles, actinic keratosis, in situ squamous cell carcinomas, superficial basal-cell carcinomas, in situ *melanoma*, lentigo maligna, lentigos, ephelids, mottled pigmentation, solar poikiloderma, solar elastosis, acne scars, skin laxity, and other dermatological surface conditions, comprising:
    topically applying a chemical peel to the skin of a subject, wherein the chemical peel consisting of:
    (i) an aqueous solvent;
    (ii) phenol;
    (iii) from 0.0001% by weight to 3.0% by weight croton oil;
    (iv) at least one saturated non-ionic ethoxylated fatty acid ester;
    (v) at least one pH adjuster; and
    (vi) at least one preservative.

20. The composition of claim 1, wherein the pH adjuster is selected from the group consisting of acetic acid, ascorbic acid, citric acid, sodium citrate, tartaric acid, ammonium hydroxide, and mixtures thereof.

21. The composition of claim 1, wherein the preservative is benzyl alcohol, ethylhexylglycerin, or a combination thereof.

* * * * *